Feb. 9, 1937. C. H. FISHER Plant Pat. 233
PEACH
Filed Oct. 1, 1936
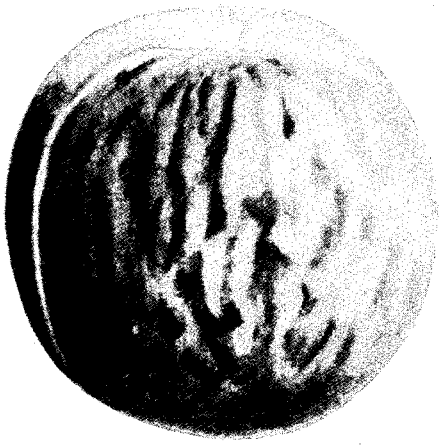
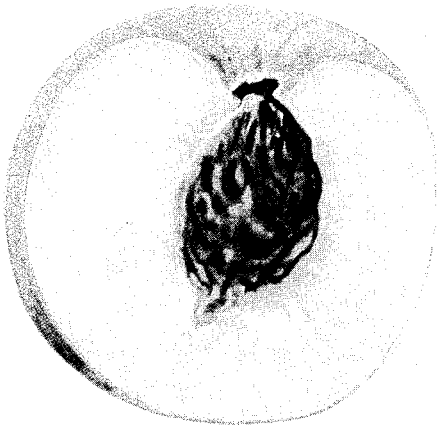
INVENTOR
Carl Howard Fisher
By Orville M. Kile
PLANT PATENT AGENT Patented Feb. 9, 1937

Plant Pat. 233

UNITED STATES PATENT OFFICE

233

PEACH

Carl Howard Fisher, Queenston, Ontario, Canada

Application October 1, 1936, Serial No. 103,605

1 Claim. (Cl. 47—62)

My discovery relates to improvements in freestone peaches of the commercial type. The principal object of my discovery is to provide an Elberta type peach with improvements in flavor and canning qualities somewhat like the Valiant but maturing much earlier than either of these varieties.

My new variety was first discovered in August, 1934, as a bud sport on one of the trees in a block of Valiants set out in 1930. One small limb near the base of this tree was bending over with 36 ripe peaches while the rest of the tree and the surrounding trees were covered with green peaches. About a month later I top-worked a two-year-old Valiant tree with buds from the sport limb, also a little later budded about 90 trees in a nursery row. The top-worked tree produced fruit in the fruiting season of 1936 and the same year the parent limb produced a very heavy crop—70 peaches to the limb, after having removed from it 91 green peaches and despite the previous removal of budwood.

In all cases, the characters of the asexually reproduced fruit are identical with those of the fruit on the original sport limb discovered in 1934.

This variety ripens about three weeks earlier than Valiant, its parent variety, and about six weeks earlier than Elberta.

The variety is more highly colored than either Elberta or Valiant, it having a dark red blush which covers about half the peach.

The accompanying paintings show a fully matured peach and the longitudinal cross section of a second fully matured peach of the new variety. The cross section shows as nearly as possible the clear yellow of the flesh which is not colored by any red around the seed.

This latter quality makes it possible to can the variety without discoloration of the syrup. Another quality which assures better canned peaches, is the habit of this peach of hanging on the tree until dead ripe.

Following is a more detailed description of the principal features of this new variety.

*The fruit*

Size:

Medium—2¼ to 2½ inches in each dimension.

Shape:

Globular; regular; cavity deep; no apex point; suture shallow but regular.

Flesh:

*Texture.*—Fine-grained; very juicy but firm.

*Color.*—Rich, clear yellow. No red is seen around pit.

Skin:

*Color.*—Very highly colored, with a deep red blush of mottled shades of red over a ground of apricot yellow.

*Texture.*—Thin but tough; easily removable from flesh of ripe fruit.

*Surface.*—Only slightly pubescent.

*Flavor.*—Pleasant, sweet.

Stone:

Free.

*Size.*—Relatively small (1¼ by ⅞ in.).

*Shape.*—Sharply pointed; plump.

*The tree*

The tree may be described as being practically identical with that of the Valiant, its parent, except as to its inherent production qualities, since no visible outward differences have been observed except possibly an added vigor in growth.

I claim:

The new and distinct variety of freestone peach tree and fruit as herein shown and described, characterized particularly by the early maturity of highly colored fruit; the very juicy but firm nature of the fruits; the absence of red coloring around the pits; and the habit of the fruits of hanging on the tree until very ripe.

CARL HOWARD FISHER.